US012727822B2

(12) United States Patent
Kangas et al.

(10) Patent No.: US 12,727,822 B2
(45) Date of Patent: Sep. 8, 2026

(54) CONFORMABLE WEARABLE DEVICE WITH DEFORMABLE SHAPE

(71) Applicant: Oura Health Oy, Oulu (FI)

(72) Inventors: Mika Petteri Kangas, Oulu (FI); Antti Kalevi Lämsä, Oulu (FI); Heikki Juhani Huttunen, Haukipudas (FI); Heli Tuulia Koskimaki, Oulu (FI); Miia Nikkila, Oulu (FI); Erin Turkoglu, Helsinki (FI); Miika Kanste, Oulu (FI); Sanna Rousu, Oulu (FI); Hannu Koivisto, Oulu (FI)

(73) Assignee: Oura Health Oy, Oulu (FI)

( * ) Notice: Subject to any disclaimer, the term of this patent is extended or adjusted under 35 U.S.C. 154(b) by 301 days.

(21) Appl. No.: 18/455,216

(22) Filed: Aug. 24, 2023

(65) Prior Publication Data

US 2025/0064398 A1 Feb. 27, 2025

(51) Int. Cl.

| | |
|---|---|
| ***A61B 5/00*** | (2006.01) |
| ***A61B 5/0205*** | (2006.01) |
| ***A61B 5/024*** | (2006.01) |
| ***A61B 5/0533*** | (2021.01) |

(52) U.S. Cl.

CPC .......... *A61B 5/6826* (2013.01); *A61B 5/0002* (2013.01); *A61B 5/02055* (2013.01); *A61B 5/02416* (2013.01); *A61B 5/0533* (2013.01); *A61B 2562/164* (2013.01)

(58) Field of Classification Search

CPC . A61B 5/6826; A61B 5/0002; A61B 5/02055; A61B 5/02416; A61B 5/0533; A61B 2562/164; A61B 5/14552

See application file for complete search history.

(56) References Cited

U.S. PATENT DOCUMENTS

| | | | | |
|---|---|---|---|---|
| 10,898,084 B2 * | 1/2021 | Khine | .................. | A61B 5/6824 |
| 2002/0052568 A1 * | 5/2002 | Houser | ................. | B60R 22/001 602/26 |
| 2012/0302889 A1 * | 11/2012 | Rajan | .................. | A61B 5/6828 600/455 |
| 2015/0164422 A1 * | 6/2015 | Lee | ...................... | A61B 5/6831 600/300 |
| 2016/0166161 A1 * | 6/2016 | Yang | .................. | A61B 5/02427 600/476 |
| 2017/0281082 A1 * | 10/2017 | Khine | ................ | A61B 5/02055 |
| 2023/0270384 A1 * | 8/2023 | Apoorv | ................ | A61B 5/6826 600/301 |

* cited by examiner

*Primary Examiner* — Jonathan T Kuo
(74) *Attorney, Agent, or Firm* — ArentFox Schiff LLP

(57) ABSTRACT

Systems and devices for a conformable wearable device are described. The wearable device may include a sensor module comprising one or more sensors configured to acquire physiological data from a user. In some cases, the wearable device may include a deformable material coupled with the sensor module and configured to transition between a planar orientation in an unworn state and a non-planar orientation in a worn state and a flexible material that at least partially encases the sensor module and the deformable material. The deformable material may be configured to at least partially conform to a body part of the user to bring the sensor module into contact with the body part of the user when the deformable material is in the worn state. In some cases, the deformable material is further configured to retain the non-planar orientation after being conformed to the body part of the user.

20 Claims, 5 Drawing Sheets

CONFORMABLE WEARABLE DEVICE WITH DEFORMABLE SHAPE

FIELD OF TECHNOLOGY

The following relates to wearable devices and data processing, including a conformable wearable device with deformable shape.

BACKGROUND

Some wearable devices may be configured to collect physiological data from users, including heart rate, motion data, temperature data, photoplethysmogram (PPG) data, and the like. Wearable devices may be manufactured using form factors that limit a quantity of skews and sizes of the wearable device. The wearable device may fit too loose or too tight depending on the fit of the wearable device. As such, conventional techniques for manufacturing a wearable device may be improved.

DETAILED DESCRIPTION

Figure 1:
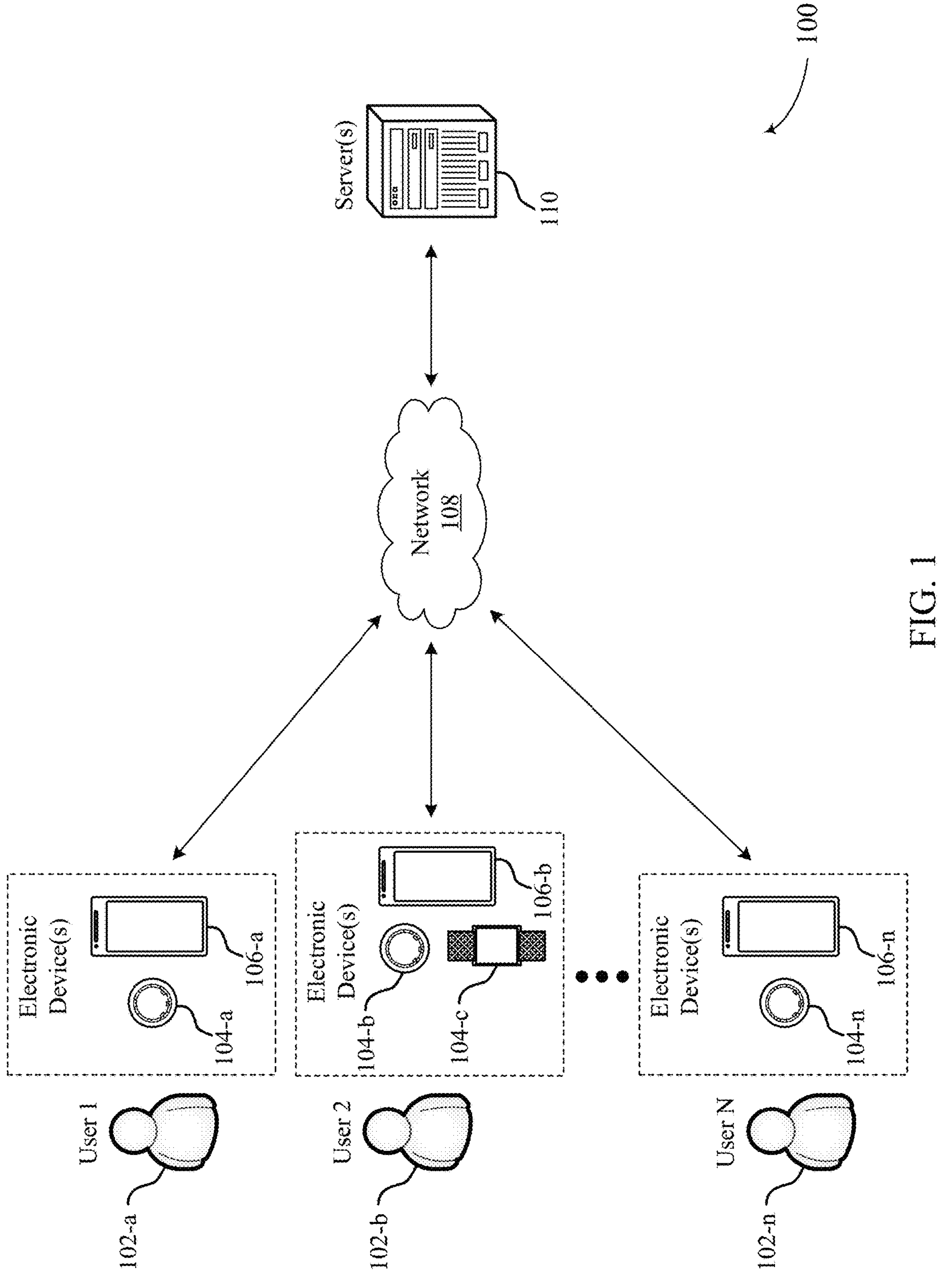
FIG. 1 illustrates an example of a system that supports a conformable wearable device with deformable shape in accordance with aspects of the present disclosure.

Due to manufacturing and cost limitations, there are a limited number of discrete ring sizes that are available to users. The sizes of the ring may depend on the size of the ring form-factor used to manufacture the ring. Manufacturing half sizes of the ring may result in too many unique stock keeping units (SKUs) and may increase tooling, manufacturing, and packing costs. As such, the ring may fit too loose or too tight for a particular user. This limitation may cause inaccurate measurements, increased power consumption, or decreased comfort. In addition, sample rings of various sizes may be sent to the user in order to find the best ring fit and match the anatomy of the user to the size of the rings. Such limitations may result in increased overhead and processing costs associated with manufacturing the sample rings to send to the user.

An inaccurate fit of the ring may affect the ability of the wearable device to efficiently and accurately acquire physiological data. Moreover, wearing a ring that isn't the right size may result in inaccurate physiological data readings, which may lead to a distorted picture of the user's overall health, as well as increased power consumption and decreased battery life. In other cases, manufacturing the ring to be a fully round metal structure may not allow the ring to be breakable in case of accidents or emergencies that may cause damage to the finger.

Accordingly, to facilitate improved user experience for users of the wearable device and improved physiological measurements, aspects of the present disclosure are directed to a conformable wearable device with a deformable shape to reduce the manufacturing costs and improve the fit of the device. The wearable device is manufactured in one size and manufactured as a straight piece rather than in ring form. The wearable device may be molded by the user when using it for the first time. For example, the wearable device may include a deformable material that transitions the wearable device from the straight, flat piece in a planar configuration to a non-planar configuration that conforms to a body part of the user. In some examples, the deformable material may at least partially wrap around a body part of the user, bend along a skin surface of the body part of the user, adhere to the skin surface of the body part the user, or a combination thereof the In some cases, based on the size (e.g., circumference) of the user's body part, the edges of the piece may overlap after rolling around the wearable device, form a gap between the edges, or align. In some cases, the design of the wearable device may enable the wearable device to be reusable and/or easily removed such that the wearable device may be breakable or safely removable in case of accidents or emergencies.

For example, the wearable device may include a deformable material that is coupled with a sensor module and is configured to transition between the straight, planar orientation in an unworn state to a non-planar orientation in the worn state. The sensor module may include one or more sensors to acquire the physiological data from the user. The deformable material may be configured to wrap at least partially conform to the body part of the user to bring the sensor module into contact with the user's body part. The wearable device may further include a flexible material that at least partially encases the sensor module and the deformable material.

By using a wearable device that begins in a straight, flat orientation, and then forms around the user's body part, the manufacturing costs may be improved by reducing the number of SKUs needed to stock the wearable device. Similarly, by using a wearable device that conforms to the body part of the user, the fit of the wearable device may be improved through the use of a deformable material that allows the wearable device to adapt to the anatomy of the body part which may lead to more accurate physiological data measurements based on the personalized, improved fit, thereby increasing the efficiency and accuracy of the signal.

Aspects of the disclosure are initially described in the context of systems supporting physiological data collection from users via wearable devices. Aspects are then described in the context of wearable devices in planar and non-planar orientations that relate to a conformable wearable device with deformable shape.

FIG. 1 illustrates an example of a system 100 that supports a conformable wearable device with deformable shape in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight." or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state: 2) circadian rhythms: 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks," 12 day rhythms could be used): 5) multi-day ovarian rhythms in women and spermatogenesis rhythms in men: 6) lunar rhythms (relevant for individuals living with low or no artificial lights): and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for implementing a wearable device 104 that starts off in a straight, flat, planar orientation and then conforms to the body part of the user. The wearable device 104 may include a sensor module comprising one or more sensors configured to acquire physiological data from a user and a deformable material coupled with the sensor module and configured to transition between a planar orientation in an unworn state and a non-planar orientation in a worn state. The deformable material may be configured to at least partially conform to the body part of the user to interface with the body part of the user such that the one or more sensors are in proximal contact to the body part of the user in the worn state. For example, the deformable material may be configured to at least partially wrap around the body part of the user and retain the circular orientation such that the sensor module is brought into contact with the body part of the user. In other examples, the deformable material may be configured to bend along a surface of the body part, adhere to the skin surface of the body part, or both such that the sensor module is brought into contact with the body part of the user.

In some cases, the wearable device 104 may include a flexible material that at least partially encases the sensor module and the deformable material. In such cases, the fit of the wearable device may be improved through the use of a deformable material. By using a deformable material that allows the wearable device to adapt to the anatomy of the body part, the wearable device 104 may perform more accurate physiological data measurements based on the personalized and improved fit, thereby increasing the efficiency and accuracy of the signal as compared to other conventional jewelry. For example, the measurement points for electronics and optics may be arranged to be in proximal contact to the body part of the user, thereby improving the quality of the measurements as the measurements may not be as sensitive to rotation.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
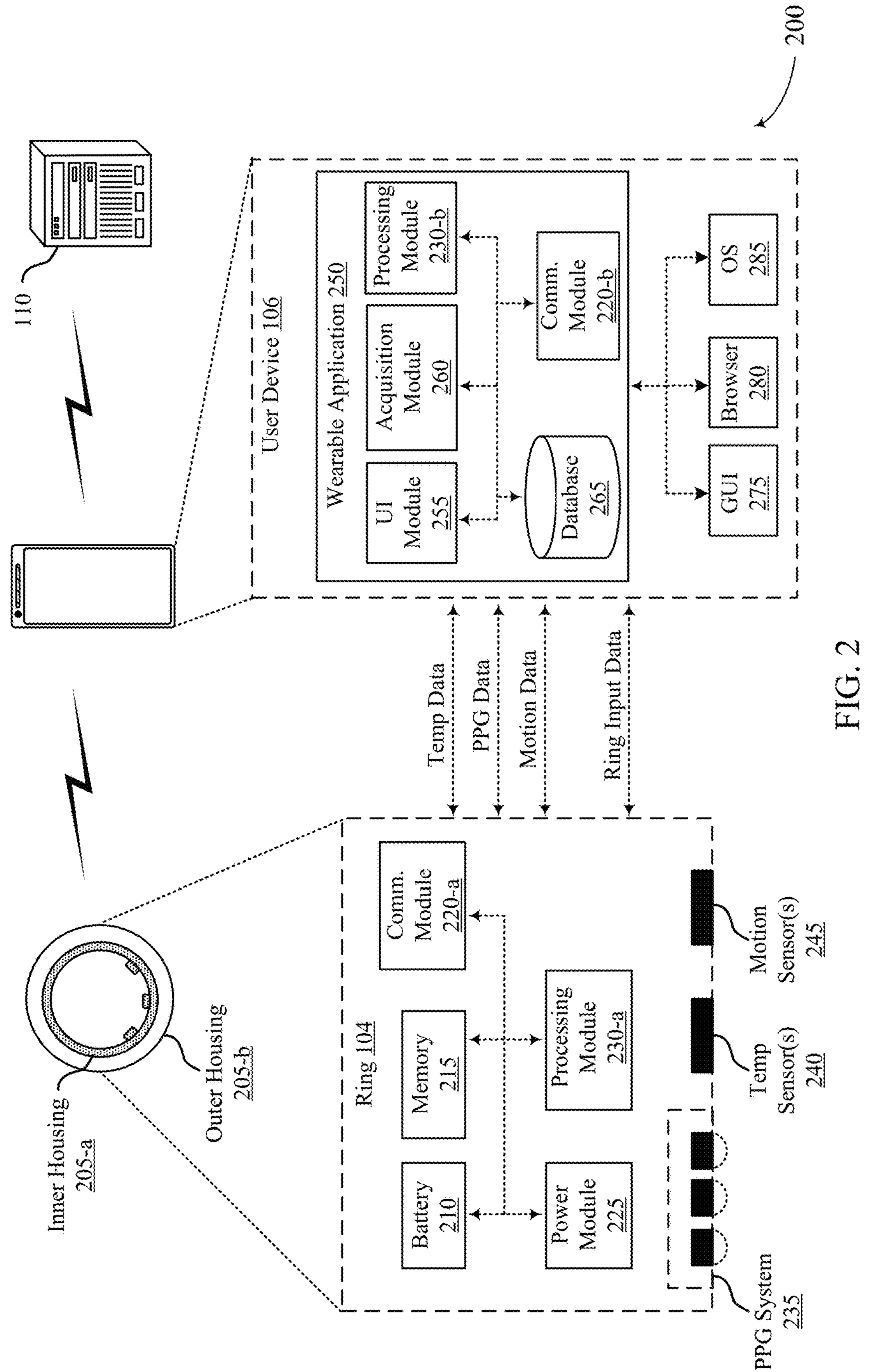
FIG. 2 illustrates an example of a system that supports a conformable wearable device with deformable shape in accordance with aspects of the present disclosure.

FIG. 2 illustrates an example of a system 200 that supports a conformable wearable device with deformable shape in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate (s) from water and/or other chemicals.

The outer housing 205-*b* may be fabricated from one or more materials. In some implementations, the outer housing 205-*b* may include a metal, such as titanium, which may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage (s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support a wearable device that starts off in a planar orientation and then conforms to the body part. In particular, techniques described herein support a wearable device 104 as described with reference to FIG. 1. For example, a wearable device 104 may include an inner housing 205-*a* configured to house a sensor module that includes one or more sensors that are configured to acquire physiological data from a user 102. The one or more sensors of the wearable device 104 may obtain physiological measurements from the user (e.g., temperature sensors, additional LED-PD sensors used for measuring heart rate, oxygen saturation, one or more sensors that a device may use to detect whether a user is asleep, galvanic sensors, or the like).

In some cases, the one or more sensors of the wearable device 104 are configured to acquire the physiological data from the user based on arterial blood flow, temperature, etc. In some implementations, the one or more sensors of the wearable device 104 are configured to acquire the physiological data (e.g., including PPG data) from the user based on blood flow that is diffused into the microvascular bed of skin with capillaries and arterioles. The one or more sensors of the wearable device 104 may be an example of photodetectors from the PPG system 235, temperature sensors 240, motion sensors 245, galvanic sensors, and other sensors.

As described herein, the wearable device of the system 200 may include a deformable material that is coupled with the sensor module and configured to transition between a planar orientation in an unworn state and a non-planar orientation in a worn state. By integrating a deformable material into the wearable device 104, the deformable material may bring the sensors in contact with the body part to perform the measurements as the deformable material conforms to the body part and forms an interference fit around the body part of the user (e.g., brings the sensor module in contact with the body part in the worn state). In some cases, the deformable material may retain the wearable device in the non-planar orientation after being at least partially wrapped around the body part of the user. The wearable device 104 may also include a flexible material that at least partially encases the sensor module and the deformable material.

While much of the present disclosure describes one or more components in the context of a wearable ring device, aspects of the present disclosure may additionally or alternatively be implemented in the context of other wearable devices. For example, in some implementations, the one or more components described herein may be implemented in the context of other wearable devices, such as bracelets, watches, necklaces, piercings, stickers, patches, and the like. For example, the wearable device 104 may surround a finger, toe, wrist, ankle, earlobe or other parts of the ear, or the like of a user. In some examples, the wearable device 104 may be adhered to the chest, the head, the arm, the leg, the back, and the like of the user.

Figure 3A:
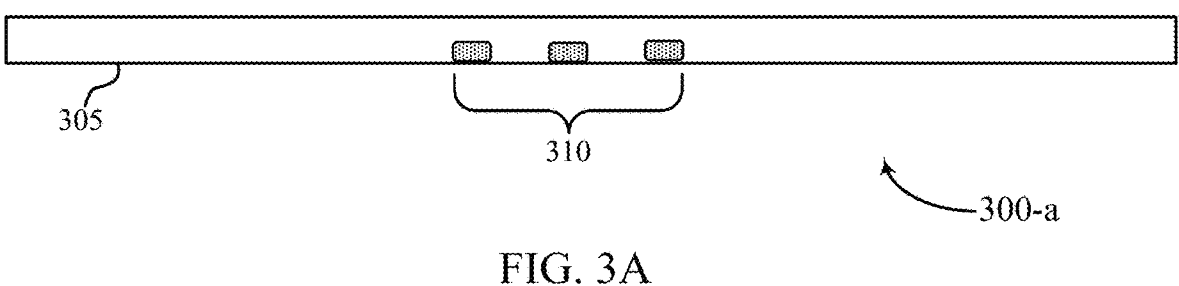
FIG. 3A shows an example of a wearable device in a planar orientation that supports a conformable wearable device with deformable shape in accordance with aspects of the present disclosure.

FIG. 3A shows an example of a wearable device 300-*a* in a planar orientation that supports a conformable wearable device with deformable shape in accordance with aspects of the present disclosure. The wearable device 300-*a* may implement, or be implemented by, aspects of the system 100, system 200, or both. For example, the wearable device 300-*a* may illustrate examples of a wearable device 300-*a* with a deformable shape as described with reference to FIGS. 1 and 2.

The wearable device 300-*a* may include a sensor module 310. The sensor module 310 may include one or more sensors configured to acquire physiological data from the user. In such cases, the wearable device 300-*a* may collect data, such as physiological data, from a user that can be used to determine health and wellness information for the user. For example, the wearable device 300-*a* may collect the data via the sensor module 310 that couples with (e.g., interface with, contact) the skin of the user. The reliability (e.g., accuracy) of the data collected by the wearable device 300-*a* may be contact-dependent, meaning that the reliability may vary with the contact between the wearable device 300-*a* and the skin of the user. But the contact between the wearable device 300-*a* and the skin of the user may be inconsistent (e.g., due to changes in position, changes in girth of the body part, differences in body part shapes, rotation of the wearable device 300-*a*, and the like).

In some cases, skin contact between the user's body part and the wearable device 300-*a* may vary due to a gap between the user's body part and the wearable device 300-*a*, a poorly fit wearable device 300-*a*, or both. Changes in skin contact against the user's body part may affect physiological measurements. For example, the changes in skin contact may cause inaccuracy in the physiological measurements and higher battery consumption. In some examples, the wearable device 300-*a* may move around the user's body part (e.g., finger, toe, wrist and the like), causing rotation of the wearable device 300-*a* and losing contact between the sensor module 310 that may affect the physiological measurements.

Use of unreliable data collected while the contact between the wearable device 300-*a* is poor may result in inaccurate health and wellness information for the user. For example, using data while the contact between the wearable device 300-*a* and the user changes may result in inaccurate physiological data readings, which may lead to a distorted picture of the user's overall health, as well as increased power consumption and decreased battery life.

Accordingly, to facilitate improved physiological measurements and improved fit, aspects of the present disclosure are directed to a one-size-fits-all wearable device 300-*a* that is manufactured as a straight, flat piece that may be custom-fitted to the body part of the user and adhered to the body part. In some examples, the wearable device 300-*a* may be custom-fitted to the finger and formed around the finger of the user rather than manufactured as a ring-form. In such cases, an amount of skews in SKUs may be limited by manufacturing a single SKU and reducing a quantity of different sizes of the wearable device 300-*a* in storage. The wearable device 300-*a* may be manufactured as the straight, planar piece of material 305 such that the structure of the wearable device 300-*a* may allow for the wearable device 300-*a* to be molded around the user's finger, attached to any part of the body of the user, breakable in case of accidents or emergencies, and the like.

The wearable device 300-*a* may include the material 305 that is configured to transition between an unworn state in a planar orientation and a worn state in a non-planar orientation. The material 305 of the wearable device 300-*a* may be configured to extend in the planar orientation in the unworn state (e.g., unmounted off the body part of the user). For example, the material 305 may be in a straight (e.g., flat)

position when the wearable device 300-*a* is in the unmounted state (e.g., open state) off of the body part of the user.

The material 305 may be formed from a material that may enable the wearable device 300-*a* to change shape while the wearable device 300-*a* transitions from the unworn state in the planar orientation to the worn state in the non-planar orientation. For example, the material 305 may include a deformable material, a flexible material, or both configured to transition the wearable device 300-*a* between the planar orientation in the unworn state and the non-planar orientation in the worn state. The material properties may be such that the wearable device 300-*a* bends into the non-planar orientation and then remains in that shape unless forcefully removed from the body part of the user. In some examples, the properties may be such that the wearable device 300-*a* at least partially wraps around the finger of the user into the non-planar (e.g., circular) orientation and then remains in that shape unless forcefully opened back up.

Figure 3B:
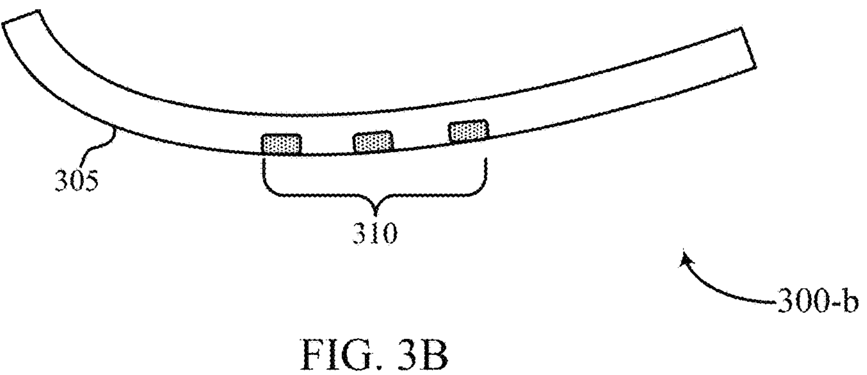
FIG. 3B shows an example of a wearable device in a non-planar orientation that supports a conformable wearable device with deformable shape in accordance with aspects of the present disclosure.

FIG. 3B illustrates an example of a wearable device 300-*b* in a non-planar orientation that supports a conformable wearable device with deformable shape in accordance with aspects of the present disclosure. The material 305 may be configured to conform to a body part of the user after being placed on (e.g., attached to) the body part of the user when the wearable device 300-*b* is in the worn state. For example, the material 305 may be in the non-planar orientation when the wearable device 300-*b* is in the worn state on the body part of the user.

During a first use of the wearable device 300-*b*, the wearable device 300- may be molded by the user onto the body part of the user. For example, the wearable device 300-*c* may be formed around or along the body part of the user to provide optimal contact between the sensor module 310 and the body part. In such cases, the sensor module 310 may perform accurate and efficient physiological measurements based on the proximal contact to the body part of the user.

In some cases, a signal quality provided by the signals of the sensor module 310 may improve based on the placement of the wearable device 300-*b*, the contact between the wearable device 300-*b* and the body part, or both. For example, the signal-to-noise ratio, perfusion index, and DC-level of the signals may improve compared to previous versions of the wearable ring device. The performance of the sensor module 310 may be consistent (e.g., similar) across all wavelengths. In some cases, an amount of stray light may decrease based on the placement of the wearable device 300-*b*, the contact between the wearable device 300-*b* and the body part, or both.

Improvements in signal quality may improve SpO2 accuracy and enable blood pressure measurements. The signal quality may improve regardless of the location and/or placement of the wearable device 300-*b* on the body of the user. For example, the signal quality may improve whether the wearable device 300-*b* is placed on the chest of the user, the head of the user, the finger of the user, and the like. In some cases, when the wearable device 300-*b* is worn on the chest, the sensor module may include one or more electrocardiogram (ECG) electrodes.

The material 305 may be deformable such that the material 305 may bend along the surface of the body part to maintain the wearable device 300-*b* on the body part of the user (e.g., in the non-planar orientation) after being placed on the body part. To conform the wearable device 300-*b* to the body part of the user, the wearable device 300-*b* may be placed over the desired position on the body part. The material 305 may be pressed onto the body part of the user such that the material 305 transitions from the planar orientation in the unworn state to the non-planar orientation in the worn state.

The material 305 may be configured to bring the sensor module 310 into contact with the body part. For example, the material 305 may be configured to form around and/or along the outer surface of the body part of the user to eliminate air gaps between the outer surface of the body part and the material 305. In such cases, the material 305 enhances the signal quality by eliminating the air gap and creating a tighter fit between the body part and the wearable device 300-*b*. In such cases, the material 305 may be disposed along the entire portion the wearable device 300-*b* to exert an even pressure on the body part along at least a portion of the body part by conforming to the outer surface of the body part and forming an interference fit along the body part when the wearable device 300-*b* is worn by the user.

As the wearable device 300-*b* transitions from the unworn state, as described with reference to FIG. 3A, to the worn state on the body part of the user, the material 305 of the wearable device 300-*b* may conform to the body part of the user such that wearable device 300-*b* curves along the surface of the body part to form an arc, a series of waves, and the like. The wearable device 300-*b* may be sized to fit to the body part of the user. For example, the wearable device 300-*b* may curve around a portion of the user's arm, leg, neck, and the like. The wearable device 300-*b* may conform to the user's chest, head, and the like to provide ample contact between the user and the wearable device 300-*b*. By enabling the wearable device 300-*b* to be attached to any part of the body besides the finger, the wearable device 300-*b* may allow for the wearable device 300-*a* to be used in medical settings (e.g., hospital settings) where rings may not be worn.

The wearable device 300-*b* may be attached to the body part of the user by one or more fastening components, as described here. For example, the wearable device 300-*b* may include a strap attached to one end of the material 305 that may be wrapped around the body part of the user and attached to the other end of the material 305. In other examples, the fastening components may be an example of an adhesive material formed on a surface of the material 305 that may be used to attach (e.g., stick) the wearable device 300-*b* to the body part of the user. In some examples, the fastening components may be an example of a tape, a glue, or both used to attach the wearable device 300-*b* to the body part of the user.

In some cases, the wearable device 300-*b* may be removed from the body part of the user by bending the wearable device 300-*b* away from the surface of the body part. In such cases, the wearable device 300-*b* may transition from the non-planar orientation to the planar orientation or non-planar orientation in the unworn state by deforming the material 305 of the wearable device 300-*c*. The material 305 may be pulled away from the body part at the ends to remove the wearable device 300-*b* from the body part. In other examples, the wearable device 300-*b* may be removed from the body part of the user by removing the strap (e.g., one or more fastening components) from the wearable device 300-*b*.

Figure 3C:
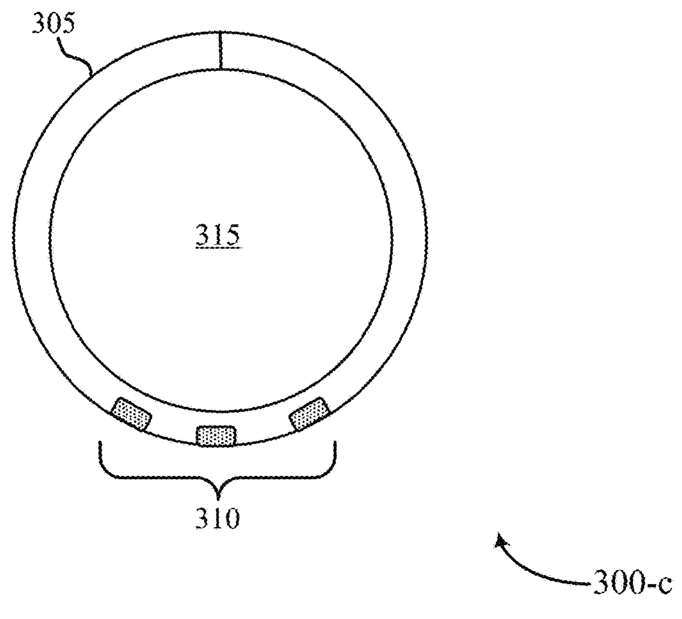
FIG. 3C shows an example of a wearable device in a rolled orientation that supports a conformable wearable device with deformable shape in accordance with aspects of the present disclosure.

FIG. 3C illustrates an example of a wearable device 300-*c* in a rolled orientation that supports a conformable wearable device with deformable shape in accordance with aspects of the present disclosure. The material 305 may be configured to at least partially wrap around the finger 315 of the user and retain the circular orientation of the wearable device

300-*c* after being wrapped around the finger 315 of the user. In such cases, the material 305 may be configured to lock the wearable device 300-*c* onto the finger 315 of the user when the wearable device 300-*c* is in the closed, worn state around the finger 315 of the user. For example, the material 305 may be in a circular orientation when the wearable device 300-*c* is in the closed state on the finger 315 of the user.

During a first use of the wearable device 300-*c*, the wearable device 300-*c* may be molded by the user onto the finger 315. For example, the wearable device 300-*c* may be a universal one-size fits all ring that may be formed around the finger 315 of the user to provide optimal contact between the sensor module 310 and the finger 315. In such cases, the sensor module 310 may perform accurate and efficient physiological measurements based on the proximal contact to the finger 315 of the user. The material 305 may be deformable such that the material 305 may provide tension around the finger 315 to maintain the wearable device 300-*c* around the finger 315 of the user (e.g., in the circular orientation) after being wrapped around the finger 315.

To at least partially wrap the wearable device 300-*c* around the finger 315 of the user, the wearable device 300-*c* may be placed over the finger 315. The material 305 may be rolled around the finger 315 of the user such that the material 305 transitions from the planar orientation in the open, unworn state to the circular, non-planar orientation in the closed, worn state. In some cases, the material 305 may include nitinol that is pre-stressed to bias into a coiled (e.g., circular) configuration around the finger 315 of the user. In some cases, the material 305 may be configured to bias into the circular orientation based on a pressure exerted on the material 305.

The material 305 may be configured to bring the sensor module 310 into contact with the finger 315. For example, the material 305 may be configured to transition to the circular orientation in the closed state such that the sensor module 310 is brought in proximal contact to the finger 315. In some cases, the material 305 may be configured to avoid interfering with measurements by the one or more sensors of the sensor module 310. In such cases, the sensor module 310 may perform measurements through the material 305. In some examples, the material 305 may be configured to interface with the sensor module 310 such that one or more antenna elements disposed within the wearable device 300-*c* may wirelessly couple the one or more components of the wearable device 300-*c* (e.g., including the sensor module 310) with a user device of the user.

The material 305 may be configured to form around the outer circumferential surface of the finger 315 of the user to eliminate air gaps between the outer circumferential surface of the finger 315 and the material 305. In such cases, the material 305 enhances the signal quality by eliminating the air gap and creating a tighter fit between the finger 315 and the wearable device 300-*c*. An air gap between the skin of the user and the wearable device 300-*c* may disturb the optical path (e.g., because the light is now coupled to the finger 315 through an additional interface) such that some or all of the light is directed away from the sensor module 310. In such cases, the material 305 may be disposed around the entire circumference of the wearable device 300-*c* to exert pressure on the finger 315 around at least a portion of the circumference of the finger 315 by conforming to the outer circumferential surface of the finger 315 and forming an interference fit around the finger 315 when the wearable device 300-*c* is worn by the user.

The material 305 may form an interference fit around the finger 315 of the user. The material 305 may be configured to interact with a surface of the finger 315 to fit the wearable device 300-*c* onto the finger 315 of the user. As the wearable device 300-*c* is wrapped around the finger 315 of the user, the material 305 may conform to an outer circumferential surface of the finger 315 to form an interference fit around the finger 315 when the wearable device 300-*c* is worn. For example, the material 305 may form a seal around the finger 315 to eliminate gaps between the wearable device 300-*c* and the finger 315 of the user such that the material 305 contacts the outer circumferential surface of the finger 315. In such cases, the material 305 may provide ample contact between the sensor module 310 and the finger 315, thereby resulting in accurate physiological measurements and enhancing the signal quality of measurements.

As the wearable device 300-*c* transitions from the open, unworn state, as described with reference to FIG. 3A, to the closed, worn state on the finger 315 of the user, the material 305 of the wearable device 300-*c* may at least partially wrap around the finger 315 of the user such that a first end of the wearable device 300-*c* aligns with a second end of the wearable device 300-*c*. In such cases, the material 305 of the wearable device 300-*c* may fully wrap around the finger 315 of the user. The material 305 may extend around a full circumference (e.g., three hundred and sixty degrees) of the wearable device 300-*c*. For example, the material may extend around a full circumference (e.g., three hundred and sixty degrees) of the finger 315 of the user. In such cases, the wearable device 300-*c* may be sized to fit around the finger 315 of the user.

In some cases, the wearable device 300-*c* may be removed from the finger 315 of the user. For example, the wearable device 300-*c* may transition to the open, unworn state by opening the wearable device 300-*c* between the two ends, and the wearable device 300-*c* transitions to the unmounted state off of the finger 315 of the user. In such cases, the wearable device 300-*c* may transition from the circular, non-planar orientation to the planar orientation by deforming the material 305 of the wearable device 300-*c*. The material 305 may be pulled apart at the ends to remove the wearable device 300-*c* from around the finger 315.

In some examples, the wearable device 300-*c* may be removed from the finger 315 of the user by sliding the wearable device 300-*c* off of the finger 315. In such cases, the wearable device 300-*c* may retain the circular orientation (e.g., non-planar orientation) after being removed from the finger 315 of the user. The wearable device 300-*c* may be reducible and reusable such that the wearable device 300-*c* may be removed and used multiple instances as well as the ability to share the wearable device 300-*c* between different users.

Figures 4A, 4B:
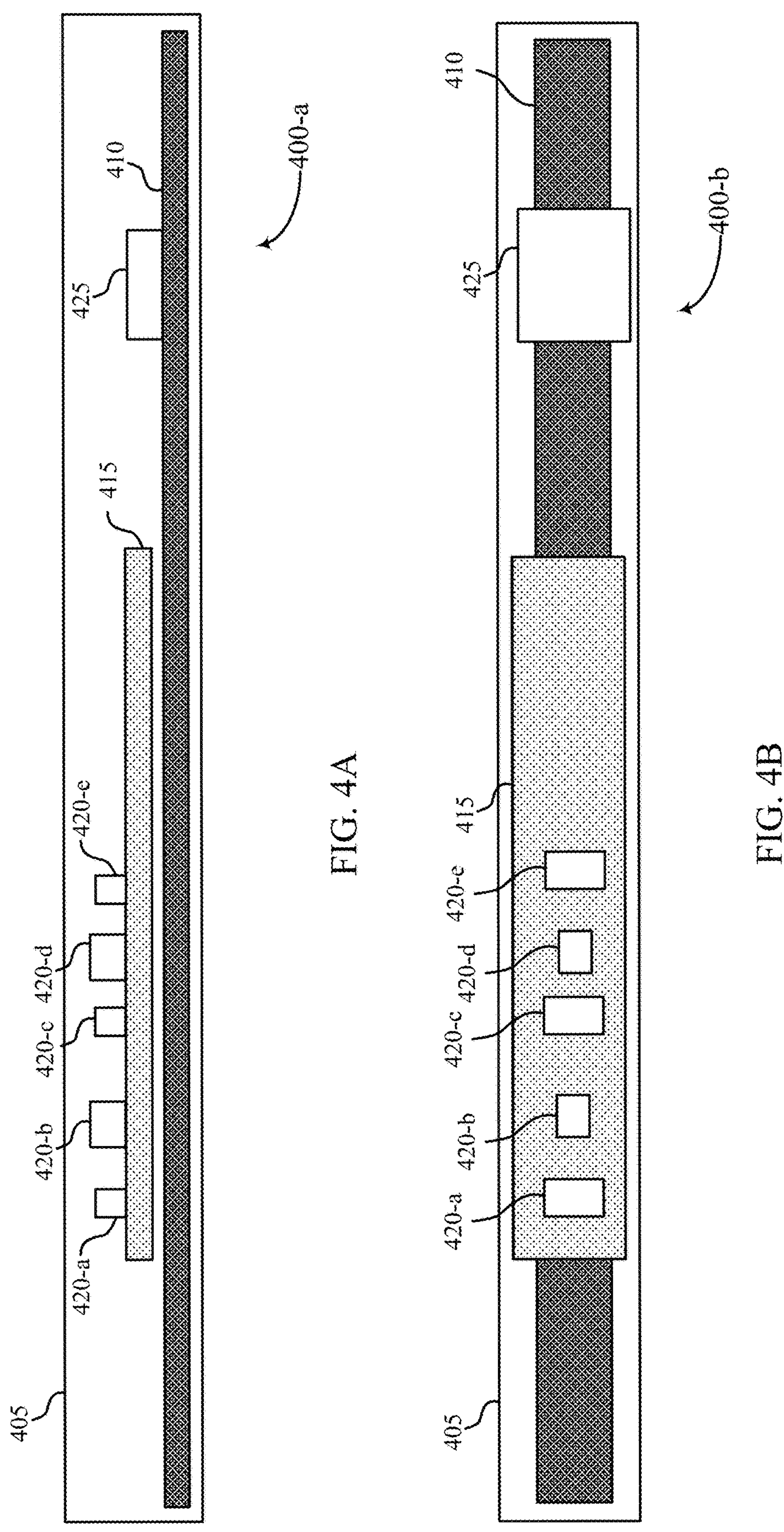
FIG. 4A shows an example of a side view of a wearable device that supports a conformable wearable device with deformable shape in accordance with aspects of the present disclosure.
FIG. 4B shows an example of a top view of a wearable device that supports a conformable wearable device with deformable shape in accordance with aspects of the present disclosure.

FIG. 4A shows an example of a side view of a wearable device 400-*a* that supports a conformable wearable device with deformable shape in accordance with aspects of the present disclosure. The wearable device 400-*a* may implement, or be implemented by, aspects of the system 100, system 200, or both. For example, the wearable device 400-*a* may illustrate examples of a wearable device 300 with a deformable shape as described with reference to FIGS. 1-3.

The wearable device 400-*a* may include a flexible material 405, a deformable material 410, and a sensor module 415. The flexible material 405 may be configured to encase the deformable material 410 and the sensor module 415. In some cases, the flexible material 405 may fully encase the deformable material 410 and the sensor module 415 (e.g., cover both the deformable material 410 and the sensor module 415). For example, the flexible material 405 may include a thickness that encompasses a thickness of the deformable material 410 and a thickness of the sensor module 415. In other examples, the flexible material 405 may partially encase the deformable material 410 and the sensor module 415 (e.g., cover the deformable material 410, cover the sensor module 415, or cover a portion of the deformable material 410 and/or a portion of the sensor module 415). In such cases, the flexible material 405 may include a thickness that encompasses the thickness of the deformable material 410 or the thickness of the sensor module 415. In some cases, the flexible material 405 may include a thickness that partially encompasses the thickness of the deformable material 410 and/or the thickness of the sensor module 415. The flexible material 405 may encase the sensors 420 and the battery 425. In some examples, the flexible material 405 may extend radially around the entire portion of the wearable device 400-*a*. The flexible material 405 may serve as housing of the wearable device 400-*a*.

The flexible material 405 may be configured to transition between the planar orientation in the worn state and the non-planar orientation in the worn state. The flexible material 405 may be configured to conform to the body part of the user to bring the sensors 420 in contact with the body part of the user. In some cases, the flexible material 405 may be configured to at least partially wrap around the finger of the user to bring the sensors 420 in contact with the finger of the user. The flexible material 405 may be plastically deformable such that an external force applied biases the flexible material 405 into the circular orientation, as described with reference to FIG. 3C. For example, the flexible material 405 may be configured to conform to an outer circumferential surface of the finger of the user to form an interference fit around the finger of the user when the wearable device 400-*a* is worn by the user. In some examples, the flexible material 405 may be configured to conform to an outer surface of the body part of the user to form an interference fit along the body party of the user when the wearable device 400-*a* is worn by the user.

In some cases, the flexible material 405 may include polyurethane, silicon, a transparent material, an opaque material, a textile material, or a combination thereof. For example, the flexible material 405 may include a transparent material disposed over the sensors 420. In some examples, the sensor module 415 may include one or more light blockers disposed adjacent to the sensors 420 to prevent stray light from entering the sensors 420 when the flexible material 405 includes the transparent material. In some cases, the flexible material 405 may be an example of a textile material that includes a decorative fabric that provides personalization, customization, and mechanical support to the wearable device 400-*a*.

In some cases, the flexible material 405 may include an opaque material. The opaque material may be removed from above the sensors 420. For example, the opaque material may be removed from above and/or on top of the sensors 420 such that the sensors 420 may perform the physiological measurements through the flexible material 405. In such cases, the opaque material may include cut outs over the sensors 420 to provide a window that allows light to travel through the flexible material 405 in order to perform the physiological measurements. In such cases, the sensors 420 may transmit and receive light through the flexible material 405.

The flexible material 405 may be configured to avoid interfering with measurements by the one or more sensors 420. In some examples, the flexible material 405 may be configured to enhance the physiological measurements performed by the sensors 420. The flexible material 405 may be configured to interface with the sensor module 415, the deformable material 410, or both such that one or more antenna elements disposed within the wearable ring device wirelessly couple one or more components of the wearable ring device with the user device associated with the user. In such cases, the flexible material 405 may not interfere with the antennas of the wearable ring device 400-*a*. The flexible material 405 may be configured to interface with the battery 425 to couple the battery 425 to the sensor module 415. In such cases, the flexible material 405 may avoid interfering with the battery 425 and enhance the performance of the battery 425.

The deformable material 410 may be encased within the flexible material 405. The deformable material 410 may extend along an entire portion of the wearable device 400-*a*. In some examples, the deformable material 410 may extend radially around a full circumference of the wearable device 400-*a* when the wearable device 400-*a* is worn by the user. In other examples, the deformable material 410 may extend partially around the circumference of the wearable device 400-*a* when the wearable device 400-*a* is worn by the user. The deformable material 410 may extend parallel along a surface of the flexible material 405. The deformable material 410 may be positioned on a portion of the flexible material 405. For example, the deformable material 410 may be coupled with the flexible material 405 and extend along a portion of the flexible material 405. In such cases, the deformable material 410 may overlap with the flexible material 405 for at least a portion of the wearable device 400-*a*.

The deformable material 410 may be configured to transition between the planar orientation in the unworn state and the non-planar orientation in the worn state, as described with reference to FIGS. 3B and 3C. For example, the deformable material 410 may be configured to at least partially wrap around the finger of the user to bring the sensor module 415 into contact with the finger of the user when the deformable material 410 is in the closed state. The deformable material 410 is further configured to retain the circular orientation after being wrapped around the finger of the user. In other examples, the deformable material 410 may be configured to conform to the body part of the user to bring the sensor module 415 into contact with the bod part of the user when the deformable material 410 is in the worn state.

The deformable material 410 may be configured to exert pressure on the flexible material 405 to bias the flexible material 405 into the circular orientation. In such cases, the deformable material 410 may serve as an external force that causes the flexible material 405 to transition from the planar orientation to the circular orientation.

The deformable material 410 may include nitinol. In some cases, the deformable material 410 may include one or more metallic strips. The metallic strips may be disposed within the deformable material 410 and configured to transition the wearable device 400-*a* from a straight position in the open, unworn state to the circular, non-planar orientation that wraps at least partially around the finger of the user. In such cases, the metallic strips may be pre-stressed to bias into the circular configuration from the flat, planar configuration (e.g., straight position). The metallic strips may be an example of nitinol strips. In some cases, the metallic strips may be configured to transition the wearable device 400-*a* from the planar orientation in the unworn state to the non-planar orientation in the worn state that conforms to the body part of the user.

In some cases, an elasticity of the deformable material 410 may change with a temperature change. For example, the deformable material 410 may store a chemical potential energy such that the chemical potential energy is activated when the deformable material 410 warms up. The flexible material 405 may heat up as the surface of the skin contacts the flexible material 405.

The elasticity of the deformable material 410 may change with temperature to change a shape, a thickness, or both of the deformable material 410 when the wearable device 400-*a* is worn by the user. In such cases, the deformable material 410 may be an example of a material that deforms at the body temperature of the user. In some examples, the deformable material 410 may include a thermal resistant material such that the deformable material 410 may become deformable at the body temperature of the user (e.g., when the wearable device 400-*a* is adhered to the body part of the user) to enable the deformable material 410 to be molded to the body part.

The deformable material 410 may be arranged to avoid interfering with measurements by the one or more sensors 420. For example, the sensors 420 may be disposed on a surface of the deformable material 410 and extend away from the surface of the deformable material 410. In some examples, the deformable material 410 may be configured to enhance the physiological measurements performed by the sensors 420 by avoiding interference with the measurements.

The deformable material 410 may be configured to interface with the sensor module 415, the battery 425, or both such that one or more antenna elements disposed within the wearable device 400-*a* wirelessly couple one or more components of the wearable device 400-*a* with the user device associated with the user. In such cases, the deformable material 410 may not interfere with the antennas of the wearable device 400-*a*. The deformable material 410 may be configured to interface with the battery 425 to couple the battery 425 to the sensor module 415. In such cases, the deformable material 410 may avoid interfering with the battery 425 and enhance the performance of the battery 425.

The wearable device 400-*a* may include an electronic substrate, such as a sensor module 415, a printed wiring board (PWB), or PCB. The sensor module 415 may have both flexible and rigid sections. In some cases, the sensor module 415 may include flexible sections that extend around at least a portion of the circumference of the wearable device 400-*a* in the non-planar, circular orientation. In some examples, the sensor module 415 may include flexible sections that extend along at least a portion of the of the wearable device 400-*a* in the non-planar orientation. Electrical components may be embedded in or on top of the sensor module 415 of the wearable device 400-*a*. The electrical components of the wearable device 400-*a* may include one or more sensors 420 (e.g., temperature sensors, light sources, photodetectors, galvanic sensors) configured to acquire physiological data associated with the user. The one or more sensors 420 of the wearable device 400-*a* may be positioned at least partially within the wearable device 400-*a*.

The sensors 420 may be configured to acquire physiological data associated with the user. For example, the wearable device 400-*a* may include a sensor 425-*a*, a sensor 420-*b*, a sensor 420-*c*, a sensor 420-*d*, and a sensor 420-*e* embedded in the wearable device 400-*a*. The sensors 420-*b*, 420-*c*, and 420-*d* may be examples of light-emitting components, and sensors 420-*a* and 420-*e* may be examples of photodetectors. In some examples, the sensor 420-*c* may be an example of a red and/or IR LED, and the sensors 420-*b* and 420-*d* may be an example of a green LED. The sensors 420 may be coupled with the battery 425.

In some cases, the sensors 420 may be disposed on the sensor module 415 at a location on the deformable material 410. For example, the sensors 420 may be disposed within the flexible material 405. The sensors 420 may extend radially around at least the same portion of the circumference of the wearable device 400-*a* that the sensor module 415 and the deformable material 410 extends around. In some cases, the sensors 420 may extend along at least the same portion of the wearable device 400-*a* that the sensor module 415 and the deformable material 410 extend along. The sensor module 415 may extend parallel along a surface of the deformable material 410. In some cases, the sensors 420 may extend perpendicular away from a surface of the sensor module 415 and towards a surface of the flexible material 405. In some cases, the sensors 420 may be disposed on a surface of the deformable material 410. In such cases, the sensors 420 may be directed away from a surface of the deformable material 410.

The battery 425 may be positioned adjacent to the sensor module 415. In some cases, the battery 425 may be disposed on the deformable material 410 and coupled with the deformable material 410. The battery 425 may include flexible sections, rigid sections, or both. In some cases, the battery 425 may include flexible sections that extend around at least a portion of the circumference of the wearable device 400-*a*. In such cases, the battery 425 may extend along at least the portion of the wearable device 400-*a*. In some cases, the wearable device 400-*a* may include one or more batteries 425. The battery 425 may be encased within the flexible material 405. In some examples, the wearable device 400-*a* may utilize a multi-device charging component to reduce the charging time for one or more wearable devices 400-*a*.

FIG. 4B illustrates an example of a top view of the wearable device 400-*b* that supports a conformable wearable device with deformable shape in accordance with aspects of the present disclosure. The sensor module 415 may be positioned on a portion of the deformable material 410. For example, the sensor module 415 may be coupled with the deformable material 410 and extend along a portion of the deformable material 410. In such cases, the sensor module 415 may overlap with the deformable material 410 for at least a portion of the wearable device 400-*a*.

The sensor module 415 may include the plurality of sensors 420. The sensors 420 may be configured to acquire physiological data and may be electrically coupled to the battery 425. In some cases, the sensors 420 may be positioned on a surface of the sensor module 415 away from (e.g., opposite of) the deformable material 410. For example, the sensors 420 may extend away from a surface of the sensor module 415 and towards the surface of the flexible material 405. The distance between each of the sensors 420 may be a same distance regardless of a size of the wearable device 400-*b*. In some cases, the placement of the sensors 420 on the sensor module 415 may be optimized to perform accurate and efficient physiological measurements.

While much of the present disclosure describes one or more components in the context of a wearable ring device, aspects of the present disclosure may additionally or alternatively be implemented in the context of other wearable devices. For example, in some implementations, the one or more components described herein may be implemented in the context of other wearable devices, such as bracelets, watches, necklaces, piercings, patches, and the like. For example, the wearable device 400-*b* may surround a finger, wrist, ankle, earlobe or other parts of the ear, or the like of a user. In some cases, the wearable device 400-*b* may be an example of a sticker that may be adhered to the finger of the user. In other examples, the wearable device 400-*b* may be an example of a sticker that may be adhered to other locations of the body such as the chest, the wrist, the neck, the back, the arm, the leg, or a combination thereof.

In some cases, the wearable device 400-*b* may be manufactured such that the wearable device 400-*b* may be manufactured step-by-step. In such cases, the electronics (e.g., including the sensor module 415) of the wearable device 400-*b* may not be designed and/or manufactured separately from the flexible material 405 and the deformable material 410. The sensors 420 may be disposed on the sensor module 415, and the sensor module 415 may be disposed on the deformable material 410. The battery 425 may be disposed on the deformable material 410. The deformable material 410 (e.g., including the battery 425, the sensor module 415, and the sensors 420) may be encased in the flexible material 405. In such cases, the wearable device 400-*b* may be manufactured as a straight, flat piece in a planar orientation that may be configured to transition to a non-planar orientation in the worn state as the wearable device 400-*b* is conformed to the body part of the user. The manufacturing process may be improved by saving time and resources while utilizing a simplified assembly process.

Figure 5A:
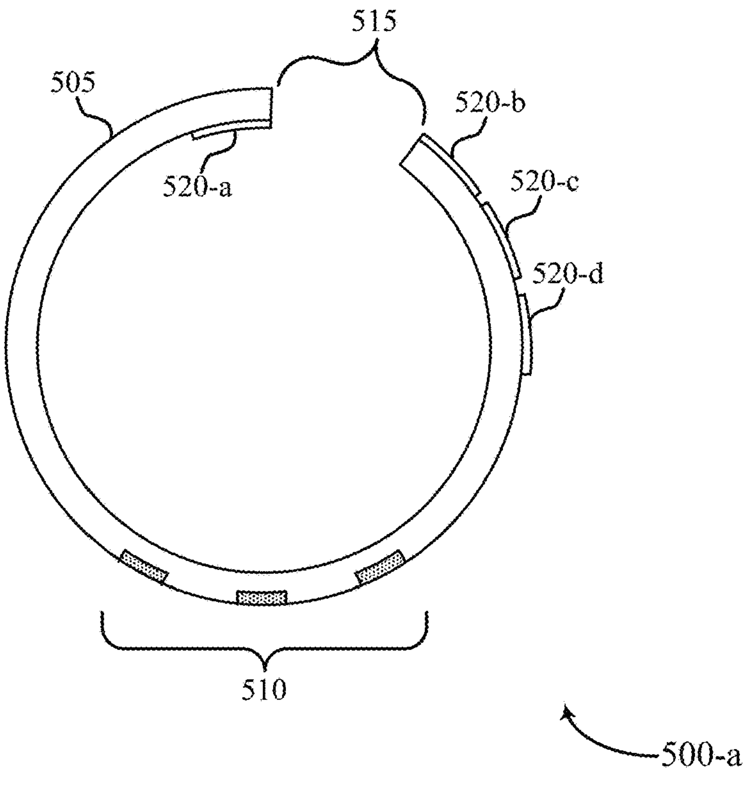
FIG. 5A shows an example of a wearable device with a gap that supports a conformable wearable device with deformable shape in accordance with aspects of the present disclosure.

FIG. 5A shows an example of a wearable device 500-*a* with a gap 515 that supports a conformable wearable device with deformable shape in accordance with aspects of the present disclosure. The wearable device 500-*a* may implement, or be implemented by, aspects of the system 100, system 200, wearable device 300, wearable device 400, or a combination thereof. For example, the wearable device 500-*a* may illustrate examples of a wearable device 500-*a* with a deformable shape as described with reference to FIGS. 1 through 4.

In some wearable devices, the wearable device 500 may fit too loose or too tight for a particular user, thereby causing inaccurate measurements, increased power consumption, decreased comfort, or a combination thereof. The inaccurate fit may affect the ability of the wearable device to efficiently and accurately acquire physiological data.

To facilitate improved physiological measurements derived from the wearable device 500-*a*, aspects of the present disclosure are directed to utilizing a wearable device 500-*a* with a deformable shape that improves the fit of the wearable device 500-*a*. For example, the wearable device 500-*a* may be molded by the user when using the wearable device 500-*a* for the first time. The wearable device 500-*a* may include a material 505 that transitions the wearable device 500-*a* from the straight, flat piece to a non-planar configuration that conforms to a body part of the user, extends at least partially around the body part of the user, or both. In some cases, based on the size (e.g., circumference) of the user's body part, the wearable device 500-*a* may form a gap 515 between edges of the material 505. The material 505 may be an example of the flexible material, the deformable material, or both as described with reference to FIGS. 1 through 4.

In some examples, the material 505 may be wrapped around the user's finger to form an interference fit around the user's finger. However, depending on the circumference of the user's finger, the material 505 may not fully wrap around the user's finger. In such cases, the gap 515 may be present in cases where there is not enough material 505 to form around the entire circumference of the user's finger. The wearable device 500-*a* may perform measurements despite the presence of the gap 515 as the sensor module 510 is brought in contact with the finger of the user when the material 505 is formed around the finger.

For example, the wearable device 500-*a* may include a gap 515 positioned away from the sensor module 510 and configured to maintain the wearable device 500-*a* at least partially wrapped around the finger of the user. In some cases, the gap 515 may be present in the circular (e.g., non-planar) orientation in the worn state around the user's finger. The material 505 may be configured to maintain the wearable device 500-*a* at least partially wrapped around the finger of the user. In some cases, the material 505 may be configured to retain the circular orientation after being wrapped around the finger of the user despite the presence of the gap 515.

The gap 515 may be arranged to avoid interfering with measurements by the one or more sensors of the sensor module 510. For example, the gap 515 may be positioned on a top surface of the user's finger rather than on an inside, bottom surface of the user's finger. In such cases, the sensors on the sensor module 510 may continue to perform measurements after being wrapped around the finger of the user. The gap 515 may be positioned away from (e.g., opposite of) the sensor module 510 to avoid interfering with the sensor measurements.

The wearable device 500-*a* may include one or more locking components 520. For example, the wearable device 500-*a* may include a first locking component 520-*a* and a second locking component 520-*b*. The locking components 520 may be disposed on a portion of the material 505. In some cases, the locking components 520 may be integrated into the material 505. The first locking component 520-*a* may be positioned at a first end of the material 505, and the second locking component 520-*b* may be positioned at a second end of the material 505. For example, the locking components 520 may extend along a portion of the material 505 such that the locking components 520 may extend from one side of the material 505 to another side of the material 505 and extend from one end of the material 505 to a distance into the material 505. The locking components 520 may be an example of a clasp component, a locking component, an adhesive material, a Velcro fastening, or a combination thereof.

In some cases, one or more locking components 520 may be included on one or both sides of the material 505 such that additional locking components 520 may be positioned next to the first locking component 520-*a* and additional locking components 520 (e.g., third locking component 520-*c* and fourth locking component 520-*d*) may be positioned next to the second locking component 520-*b*. In such cases, the various configurations or degrees of the locking components 520 may be aligned and joined to retain the wearable device 500-*a* in the closed, worn state, as described herein with reference to FIG. 5B.

The locking components 520 may be an example of the fastening components coupled with the flexible material. The first locking component 520-*a* may be an example of a hole, and the second locking component 520-*b*, the third locking component 520-*c*, and the fourth locking component 520-*d* may be an example of a protrusion configured to fit within the hole (e.g., the first locking component 520-*a*).

The wearable device 500-*a* may be customized for fingers or other body parts of various shapes and sizes. In such cases, the wearable device 500-*a* customized to a body part with a smaller circumference may include a smaller gap 515 as compared to a wearable device 500-*a* customized to a body part with a larger circumference. As the size of the body part changes (e.g., due to changes in skin temperature, stress, activity, and the like), the material 505 may deform to expand and/or contract as the body part changes shape and size, thereby increasing the comfort of the wearable device 500-*a* on the user.

For example, as the circumference of the body part increases due to an increase in temperature, the material 505 may stretch to allow the finger diameter to increase while maintaining an interference fit around the user's body part. In such cases, the distance between the two edges of the material 505 (e.g., the gap 515) may increase as the wearable device 500-*a* further opens. In other examples, as the circumference of the body part decreases, the material 505 may contract to form around the body part and the size of the gap 515 may decrease as the wearable device 500-*a* further closes.

Figure 5B:
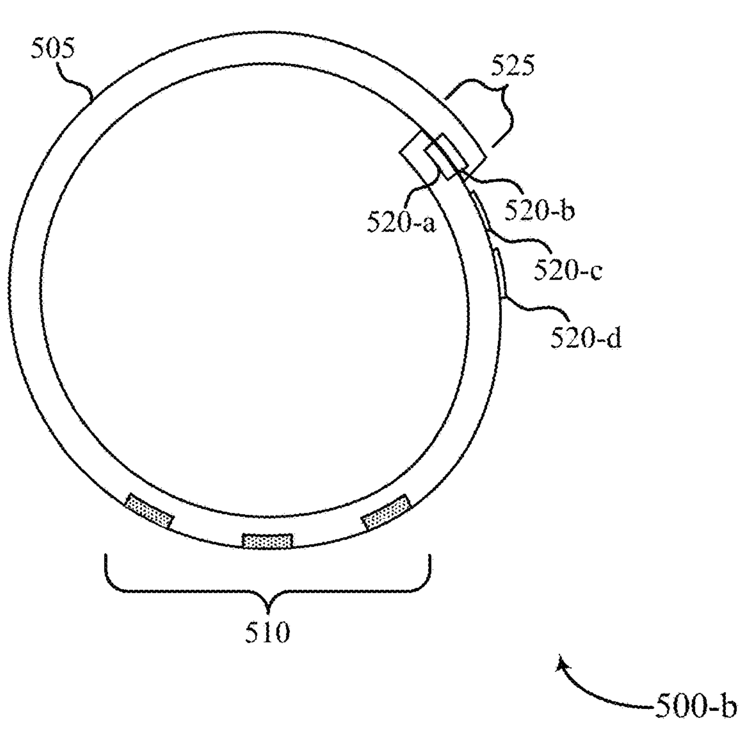
FIG. 5B shows an example of a wearable device with an overlapping portion that supports a conformable wearable device with deformable shape in accordance with aspects of the present disclosure.

FIG. 5B shows an example of a wearable device 500-*b* with an overlapping portion 525 that supports a conformable wearable device with deformable shape in accordance with aspects of the present disclosure. The material 505 may include an overlapping portion 525 in the circular orientation in the closed state. The overlapping portion 525 may be configured to further retain the wearable device 500-*b* in the circular orientation.

In some cases, the one or more locking components 520 may be disposed on the overlapping portion 525 of the material 505. The locking components 520 may be configured to transition the wearable ring device 500-*b* between an unclasped state and a clasped state. In such cases, the locking components 520 may be configured to maintain the material 505 at least partially around the finger or other body part of the user. The wearable ring device 500-*b* may be fixed and/or tightened with the locking components 520 at the end of the straight functional module. In some cases, the locking components 520 may be configured to keep the ends of the wearable device 500-*b* in contact when the overlapping portion 525 is present.

The locking components 520 may be configured to serve as an additional force and/or mechanism that retains the wearable device 500-*b* in the circular orientation after being wrapped around the user's finger or other body part. In some cases, the overlapping portion 525 may be arranged to avoid interfering with measurements by the one or more sensors of the sensor module 510. For example, the overlapping portion 525 may be positioned away from (e.g., opposite of) the sensor module 510 to avoid interfering with the sensor measurements. In some cases, the overlapping portion 525 may be positioned on a top surface of the user's finger rather than on an inside, bottom surface of the user's finger. In such cases, the sensors on the sensor module 510 may continue to perform measurements after being wrapped around the finger or other body part of the user.

In some cases, the interference fit around the user's finger or other body part may allow for varying degrees of overlap of the two ends of the wearable ring device 500-*b* depending on the circumference of the wearer's body part. For example, a wearable device 500-*b* customized to a body part with a smaller circumference may include a larger overlapping portion 525 as compared to a wearable device 500-*b* customized to a body part with a larger circumference.

To allow for changes in user's body part's shape, size, and/or girth over the course of a day, the material 505 may change shape and/or thickness to expand and contract with the changes to the user's body part. For example, as the circumference of the body part increases, the overlapping portion 525 may decrease as the wearable device 500-*b* opens up. In such cases, the locking components 520 may be adjusted such that the first locking component 520-*a* may be aligned and joined with second locking component 520-*b* rather than third locking component 520-*c* or fourth locking component 520-*d*.

In other examples, as the circumference of the body part decreases, the material 505 may contract to form around the body part and the overlapping portion may increase as the wearable device 500-*b* further closes. The locking components 520 may be adjusted to accommodate the change in body part sizes such that the first locking component 520-*a* may be aligned with third locking component 520-*c* or fourth locking component 520-*d*.

It should be noted that the methods described above describe possible implementations, and that the operations and the steps may be rearranged or otherwise modified and that other implementations are possible. Furthermore, aspects from two or more of the methods may be combined.

An apparatus is described. The apparatus may include a sensor module comprising one or more sensors configured to acquire physiological data from a user, a deformable material coupled with the sensor module and configured to transition between a planar orientation in an unworn state and a non-planar orientation in a worn state, and a flexible material that at least partially encases the sensor module and the deformable material, wherein the deformable material is configured to at least partially conform to a body part of the user to bring the sensor module into contact with the body part of the user when the deformable material is in the worn state, and wherein the deformable material is further configured to retain the non-planar orientation after being conformed to the body part of the user.

In some examples of the apparatus described herein, the deformable material may be further configured to at least partially wrap around a body part of the user, bend along a skin surface of the body part of the user, adhere to the skin surface of the body part the user, or a combination thereof.

In some examples of the apparatus described herein, the conformable wearable device comprises a wearable ring device, the deformable material may be configured to at least partially wrap around a digit of the user to bring the sensor module into contact with the digit of the user when the deformable material may be in the worn state, and the deformable material may be further configured to retain a circular orientation after being wrapped around the digit of the user.

In some examples of the apparatus described herein, the apparatus may include an overlapping portion positioned away from the sensor module in the circular orientation and arranged to avoid interfering with measurements by the one or more sensors.

In some examples of the apparatus described herein, the apparatus may include one or more locking components coupled with the flexible material and configured to transition the conformable wearable device between an unclasped state and a clasped state to retain the circular orientation.

In some examples of the apparatus described herein, the apparatus may include a gap positioned opposite the sensor module in the circular orientation and configured to maintain the wearable ring device at least partially wrapped around the digit of the user.

In some examples of the apparatus described herein, the deformable material comprises a material that may be prestressed to bias into the circular orientation.

In some examples of the apparatus described herein, the deformable material may be configured to exert pressure on the flexible material to bias the flexible material into the circular orientation.

In some examples of the apparatus described herein, the deformable material may be arranged to avoid interfering with measurements by the one or more sensors and the one or more sensors may be disposed on a surface of the deformable material.

In some examples of the apparatus described herein, the deformable material may be plastically deformable such that an external force may be applied to bias the deformable material into the non-planar orientation.

In some examples of the apparatus described herein, an elasticity of the deformable material changes with a temperature change.

In some examples of the apparatus described herein, the flexible material may be configured to interface with the sensor module, deformable material, or both such that one or more antenna elements disposed within the conformable wearable device wirelessly couple one or more components of the conformable wearable device with a user device.

In some examples of the apparatus described herein, one or more sensors may be configured to perform measurements through the flexible material.

In some examples of the apparatus described herein, the flexible material may be configured to conform to an outer surface of the body part of the user to form an interference fit around the body part of the user when the conformable wearable device may be worn by the user.

In some examples of the apparatus described herein, the flexible material comprises polyurethane, silicon, a transparent material, an opaque material, or a combination thereof.

In some examples of the apparatus described herein, the flexible material comprises a transparent material disposed on the one or more sensors, a portion of an opaque material may be removed over the one or more sensors, or both.

In some examples of the apparatus described herein, the apparatus may include one or more fastening components coupled with the flexible material and configured to attach the conformable wearable device to the body part of the user in the worn state.

In some examples of the apparatus described herein, the apparatus may include a battery, wherein the battery may be encased in the flexible material and positioned opposite the sensor module.

In some examples of the apparatus described herein, the one or more sensors comprise a light-emitting component, a photodetector, a temperature sensor, a galvanic sensor, or a combination thereof, disposed on the sensor module within the flexible material.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A conformable wearable device, comprising:

a sensor module comprising one or more light emitting components and one or more photodetectors configured to acquire photoplethysmography (PPG) data from a user;

a deformable material coupled with the sensor module and configured to transition between a planar orientation in an unworn state and a non-planar orientation in a worn state, wherein at least a portion of the sensor module is configured to deform based at least in part on a transition of the deformable material from the planar orientation to the non-planar orientation; and a flexible material that encases the sensor module and the deformable material, wherein the deformable material is configured to at least partially conform to a body part of the user to enable the one or more light emitting components and the one or more photodetectors to acquire the PPG data when the deformable material is in the worn state, and wherein the deformable material is further configured to retain the non-planar orientation after being conformed to the body part of the user.

2. The conformable wearable device of claim 1, wherein the deformable material is further configured to at least partially wrap around the body part of the user, bend along a skin surface of the body part of the user, adhere to the skin surface of the body part the user, or a combination thereof.

3. The conformable wearable device of claim 2, wherein:

the conformable wearable device comprises a wearable ring device, the deformable material is configured to at least partially wrap around a digit of the user to bring the sensor module into contact with the digit of the user when the deformable material is in the worn state, and the deformable material is further configured to retain a circular orientation after being wrapped around the digit of the user.

4. The conformable wearable device of claim 3, further comprising:

an overlapping portion positioned away from the sensor module in the circular orientation and arranged to avoid interfering with measurements by the one or more light emitting components and the one or more photodetectors.

5. The conformable wearable device of claim 3, further comprising:

one or more locking components coupled with the flexible material and configured to transition the conformable wearable device between an unclasped state and a clasped state to retain the circular orientation.

6. The conformable wearable device of claim 3, further comprising:

a gap positioned opposite the sensor module in the circular orientation and configured to maintain the wearable ring device at least partially wrapped around the digit of the user.

7. The conformable wearable device of claim 3, wherein the deformable material comprises a material that is pre-stressed to bias into the circular orientation.

8. The conformable wearable device of claim 3, wherein the deformable material is configured to exert pressure on the flexible material to bias the flexible material into the circular orientation.

9. The conformable wearable device of claim 1, wherein:

the deformable material is arranged to avoid interfering with measurements by the one or more light emitting components and the one or more photodetectors, and the one or more light emitting components and the one or more photodetectors are disposed on a surface of the deformable material.

10. The conformable wearable device of claim 1, wherein the deformable material is plastically deformable such that an external force is applied to bias the deformable material into the non-planar orientation.

11. The conformable wearable device of claim 1, wherein an elasticity of the deformable material changes with a temperature change.

12. The conformable wearable device of claim 1, wherein the flexible material is configured to interface with the sensor module, the deformable material, or both such that one or more antenna elements disposed within the conformable wearable device wirelessly couple one or more components of the conformable wearable device with a user device.

13. The conformable wearable device of claim 1, wherein the flexible material is configured to conform to an outer surface of the body part of the user to form an interference fit around the body part of the user when the conformable wearable device is worn by the user.

14. The conformable wearable device of claim 1, wherein the flexible material comprises polyurethane, silicon, a transparent material, an opaque material, or a combination thereof.

15. The conformable wearable device of claim 1, wherein the flexible material comprises a transparent material disposed on the one or more light emitting components and the one or more photodetectors, a portion of an opaque material is removed over the one or more light emitting components and the one or more photodetectors, or both.

16. The conformable wearable device of claim 1, further comprising:

one or more fastening components coupled with the flexible material and configured to attach the conformable wearable device to the body part of the user in the worn state.

17. The conformable wearable device of claim 1, further comprising:

a battery, wherein the battery is encased in the flexible material and positioned opposite the sensor module.

18. The conformable wearable device of claim 1, wherein the sensor module further comprises a temperature sensor, a galvanic sensor, or both, disposed on the sensor module within the flexible material.

19. The conformable wearable device of claim 1, wherein a position of at least one of the one or more light emitting components or the one or more photodetectors relative to the body part of the user changes based at least in part on deformation of the portion of the sensor module.

20. The conformable wearable device of claim 1, comprising:

a battery coupled with the deformable material and positioned relative to the sensor module, wherein at least a portion of the battery is configured to deform based at least in part on the transition of the deformable material from the planar orientation to the non-planar orientation.

* * * * *